(12) United States Patent
Broten et al.

(10) Patent No.: US 9,707,136 B2
(45) Date of Patent: Jul. 18, 2017

(54) EQUINE BANDAGE WRAPPER

(71) Applicant: Sally Broten, River Falls, WI (US)

(72) Inventors: Sally Broten, River Falls, WI (US); Mark Peltier, Lake Elmo, MN (US)

(73) Assignee: Sally Broten, St. Paul, MN (US)

( * ) Notice: Subject to any disclaimer, the term of this patent is extended or adjusted under 35 U.S.C. 154(b) by 100 days.

(21) Appl. No.: 14/843,627

(22) Filed: Sep. 2, 2015

(65) Prior Publication Data

US 2016/0058633 A1    Mar. 3, 2016

Related U.S. Application Data

(60) Provisional application No. 62/044,821, filed on Sep. 2, 2014.

(51) Int. Cl.
*B65H 54/58* (2006.01)
*A61F 15/00* (2006.01)
*B65H 18/02* (2006.01)

(52) U.S. Cl.
CPC .......... *A61F 15/007* (2013.01); *B65H 18/026* (2013.01); *B65H 54/585* (2013.01); *B65H 2701/177* (2013.01); *B65H 2701/37* (2013.01)

(58) Field of Classification Search
CPC .......... A61F 15/00; B65H 54/58; B65H 18/02
See application file for complete search history.

(56) References Cited

U.S. PATENT DOCUMENTS

| 3,516,618 A | 6/1970 | Reinke |
| 4,161,298 A * | 7/1979 | Davis ............ B65H 18/10 242/530.3 |
| 4,892,265 A | 1/1990 | Cox |
| 5,533,689 A * | 7/1996 | Chalfant ............ B65H 18/10 242/532.5 |
| 2002/0088893 A1 | 7/2002 | Nichols |

FOREIGN PATENT DOCUMENTS

| CA | 2009248 A1 | 8/1991 |
| DE | 10230608 A1 | 3/2003 |

OTHER PUBLICATIONS

International Search Report and the Written Opinion rendered by the International Searching Authority on Dec. 4, 2015, 28 pages.

* cited by examiner

*Primary Examiner* — Sang Kim
(74) *Attorney, Agent, or Firm* — Skaar Ulbrich Macari, P.A.

(57) ABSTRACT

An equine bandage wrapping device includes a motor with a rotating drive shaft mounted on a hinged bracket. A forked spindle coupled to the motor engages the bandage. The hinged bracket pivots in response to external force causing a torque on the hinge. The external force is supplied by the user pulling slightly against the bandage while it is secured to the forks. Such force is resisted by a spring disposed between a base plate and the underside of the floating end of the hinged bracket. If sufficient force is applied to overcome the spring force, then the electrical circuit between the motor and power source is closed, resulting in the motor turning on. The circuit is opened by removing the external force to cause the spring to return to its extended position, resulting in the motor stopping movement.

20 Claims, 18 Drawing Sheets

EQUINE BANDAGE WRAPPER

PRIORITY

This application claims the benefit of U.S. Provisional Application Ser. No. 62/044,821, filed on Sep. 2, 2014, which is hereby incorporated herein by reference in its entirety.

FIELD

The present invention relates generally to bandage winding devices and systems and, more particularly, to a motorized bandage wrapping system for horse care.

BACKGROUND

Re-usable leg wraps and bandages are frequently used for horses, especially performance and racing horses. These bandages are often applied to each of the horse's legs before specific events and are removed following completion of the event. The considerable length of each bandage results in each bandage being wound up for storage between uses.

Winding the bandages up by hand is slow, labor-intensive, inconsistent and costly. Hand-winding can also lead to long-term joint health issues similar to persons who use computers for many hours, carpenters and assembly-line workers.

Hand-crank operated winding devices are also inconvenient and only slightly less time consuming to operate because such devices require one hand to crank, leaving only one hand free to guide the bandage while its being rewound.

Motorizing the spooling process is problematic because it is desirable to use both hands to guide the bandage as it wraps on the spool. Thus operation of an on/off switch by one hand is inconvenient and presents a potentially dangerous free-spinning spool situation. Foot-actuated pedals are not desirable because they are exposed to the re-wrapping environment that may include water, dirt and heavy human/animal foot traffic.

Thus, there remains a need to provide an improved bandage wrapping device, system and method.

SUMMARY

The present invention provides a unique device, system and method that rewraps bandages quickly, neatly and tightly as compared to the conventional techniques described above.

Disclosed is a wrapping apparatus comprising a winding motor actuated by an internal micro-pressure switch that allows the user to keep two hands on the bandage ensuring a smooth and quick process. The pressure switch activates the motor to wind or turn the spool when the bandage is pulled or tugged slightly by the user. When the user releases the pressure on the bandage the pressure switch returns to the off position to stop the motor.

The pressure switch eliminates the need for a foot switch or other on/off means, and thus makes for an efficient, clean and safe environment in the re-wrapping area. This can reduce or eliminate the physical stress on hands and wrists that can cause nerve, tendon and ligament damage and long-term injury such as Carpal Tunnel and Tarsal Tunnel Syndrome while manually re-wrapping. This makes the re-wrapping process faster and more enjoyable, which can motivate the consumer to use "non-disposable" environmentally responsible wrapping materials.

Also disclosed is an equine bandage wrapping device including a motor with a rotating drive shaft mounted on a hinged bracket. A forked spindle coupled to the motor engages the bandage. The hinged bracket pivots in response to external force causing a torque on the hinge. The external force is supplied by the user pulling slightly against the bandage while it is secured to the forks. Such force is resisted by a spring disposed between a base plate and the underside of the floating end of the hinged bracket. If sufficient force is applied to overcome the spring force, then the electrical circuit between the motor and power source is closed, resulting in the motor turning on. The circuit is opened by removing the external force to cause the spring to return to its extended position, resulting in the motor stopping movement.

The disclosure includes an equine bandage wrapping device. The device includes a base plate and a frame mounting plate pivotally coupled to a base plate. The frame mounting plate includes a first side pinned to the base plate and an opposing free side. The free side is pivotal between a first position and a second position. A spring is disposed between the base plate and the frame mounting plate. The spring is compressed when the frame mounting plate pivots from the first position to the second position. An electric motor is disposed on the frame mounting plate. A switch is electrically coupled to the motor and mechanically coupled to the frame mounting plate such that the switch is closed to complete an electrical circuit and turn on the electric motor when the frame mounting plate pivots from the first position to the second position and such that the switch is activated to open an electric circuit which turns off the electric motor when the spring is uncompressed due to pivoting of the frame mounting plate from the second position to the first position. A forked spindle assembly is coupled to the electric motor that is configured to wind up an equine bandage as the motor turns.

Also disclosed is a method of wrapping an elongated bandage having first and second opposing ends. The method includes engaging a bandage with a forked spindle adjacent a first end of the bandage. A tension force is applied to the bandage to cause a motor to rotate the forked spindle while the tension force is applied. The tension force is withdrawn from the bandage to stop the motor from rotating the forked spindle.

The tension force can be withdrawn from the bandage when the bandage is finished winding up into a spool on the forked spindle, or when the user decides to stop the winding process.

The application of the tension force to the bandage can be in a direction normal to an axis of rotation of the forked spindle. The tension force in certain embodiments causes a motor mounting frame to pivot about an axis that is parallel to an axis of rotation of the forked spindle. In certain embodiments applying the tension force to the bandage causes a pressure switch to close an electrical circuit that provides power to the motor.

Withdrawing the tension force to the bandage causes a pressure switch to open an electrical circuit that provides power to the motor.

The motor can be disposed inside of an enclosure such that at least a portion of the forked spindle protrudes from the enclosure. The enclosure can be mounted on one of a vertical surface and a horizontal surface.

Further disclosed is an equine bandage wrapping system. The system includes a base plate and a frame mounting plate pivotally coupled to a base plate. A resilient means, such as a spring or gasket, is disposed between the base plate and the frame mounting plate for biasing the free side of the frame mounting plate away from the base plate. An electric motor is disposed on the frame mounting plate. A switch is electrically coupled to the motor and mechanically coupled to the frame mounting plate such that the switch is activated to complete an electrical circuit and turn on the electric motor when a free end of the frame mounting plate pivots towards the base plate and such that the switch is deactivated to open an electric circuit to turn off the electric motor when the free end of the frame mounting plate pivots away from the base plate. A forked spindle assembly is coupled to the electric motor that is configured to wind up an equine bandage as the motor turns. A housing can be disposed over the base plate that encloses the motor, the switch, the resilient means and the frame mounting plate, wherein at least a portion of the forked spindle assembly externally protrudes from the housing.

The above summary is not intended to limit the scope of the invention, or describe each embodiment, aspect, implementation, feature or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
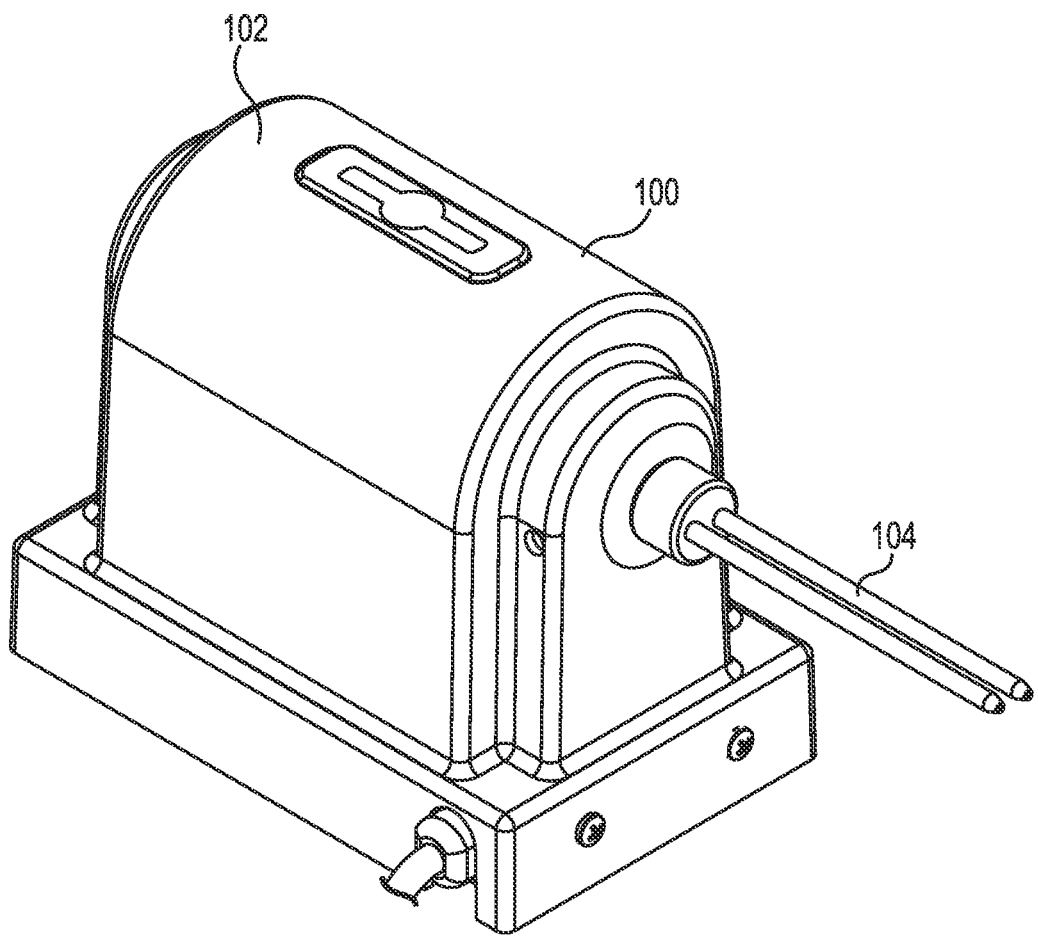
FIG. 1 is a perspective view of a re-wrapping device for animal leg bandages according to certain example embodiments.
Figure 2:
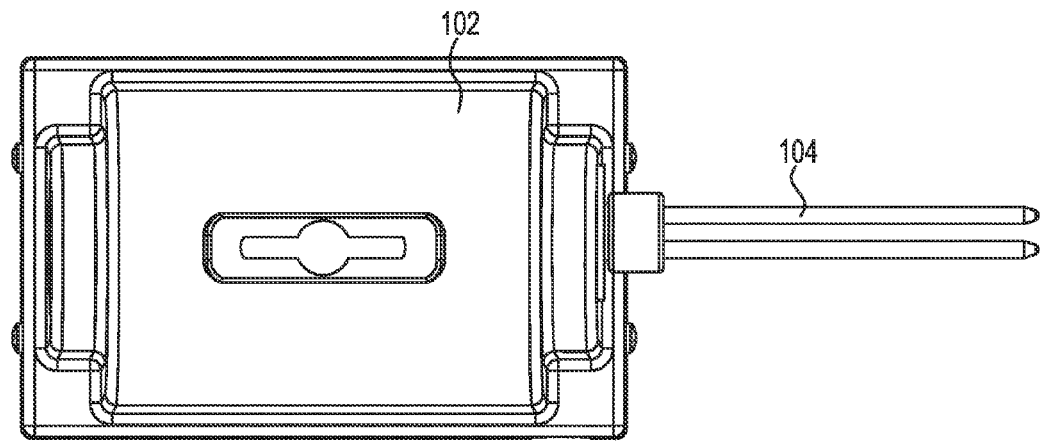
FIG. 2 is a top view of a re-wrapping device for animal leg bandages according to certain example embodiments.
Figure 3:
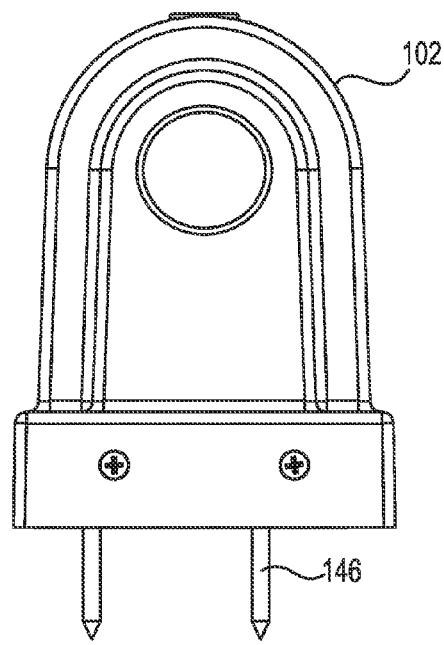
FIG. 3 is an end view of a re-wrapping device for animal leg bandages according to certain example embodiments.
Figure 4:
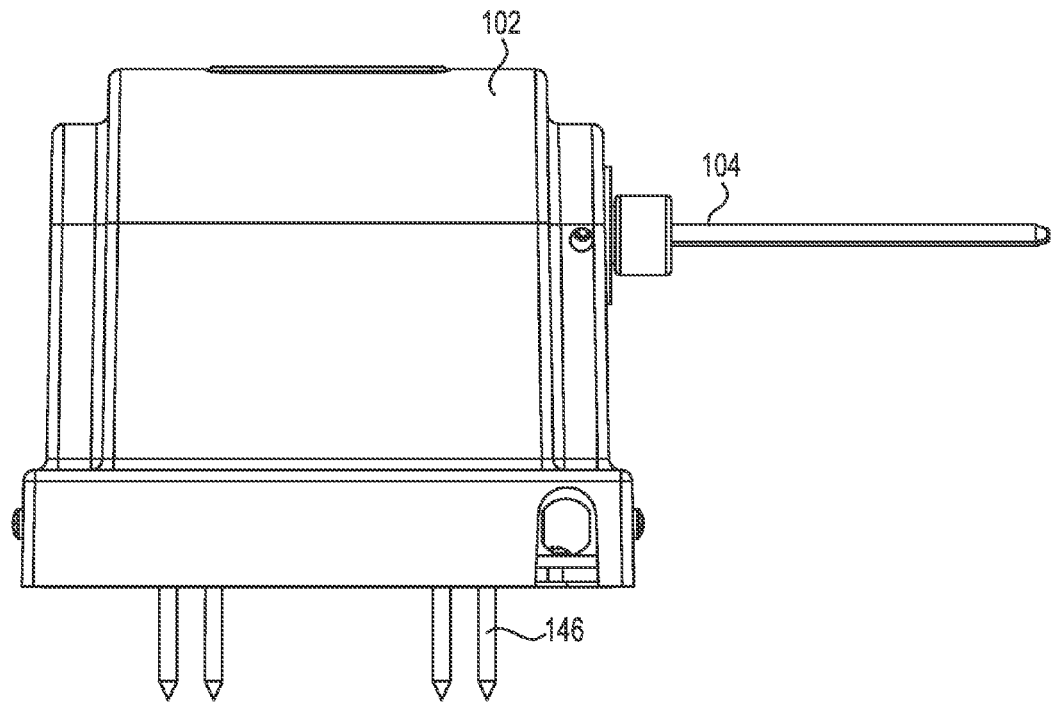
FIG. 4 is a side view of a re-wrapping device for animal leg bandages according to certain example embodiments.
Figure 5:
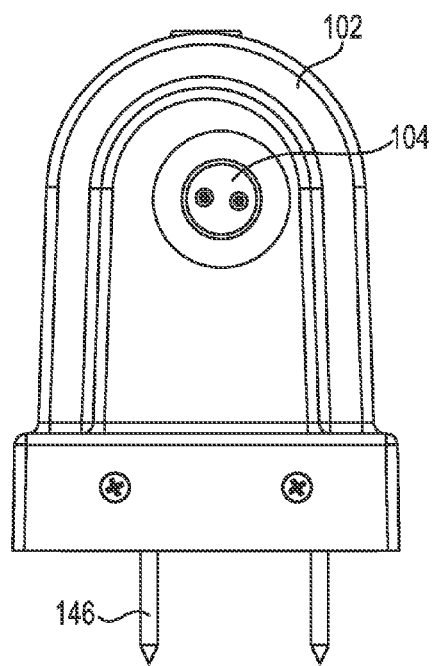
FIG. 5 is a spindle end view of a re-wrapping device for animal leg bandages according to certain example embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Referring to FIGS. 1-5, the wrapping apparatus 100 generally comprises an electric motor disposed inside of a housing 102 with a forked spindle assembly 104 that protrudes outwards from the housing 102. The spindle 102 is coupled to the motor's output shaft so that the motor turns the spindle when activated.

As will be described in detail later herein, the motor is mounted so that it can pivot in response to pressure being applied laterally (i.e. in a direction normal to the direction of the longitudinal length of the spindle forks). A pressure switch is coupled to the motor assembly so that the pivoting of the motor causes the motor to activate and turn the spindle. The motor pivot is spring-mounted so that releasing pressure on the spindle forks causes the motor to turn off.

Figure 6:
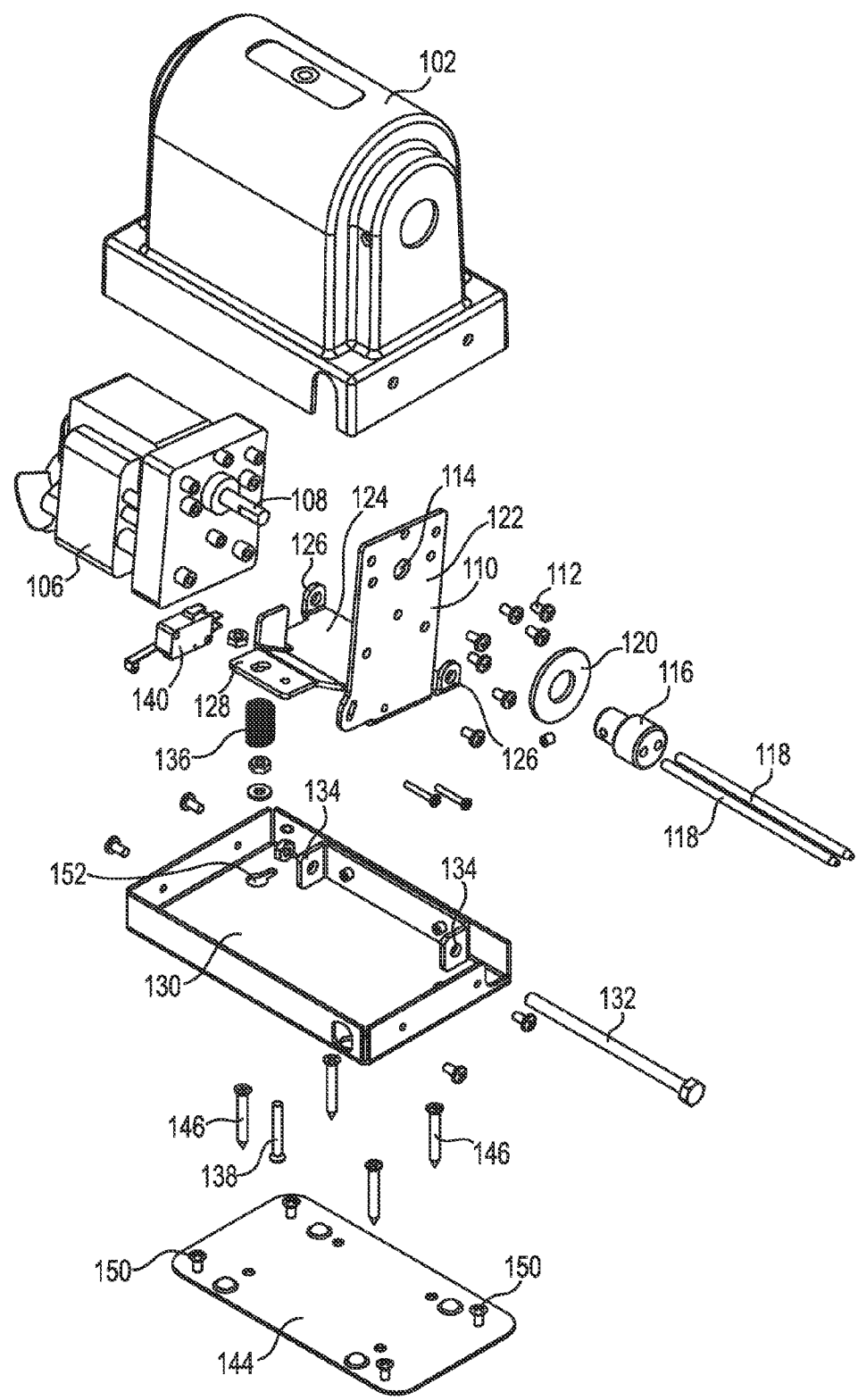
FIG. 6 is an exploded assembly view of a re-wrapping device for animal leg bandages according to certain example embodiments.
Figure 7:
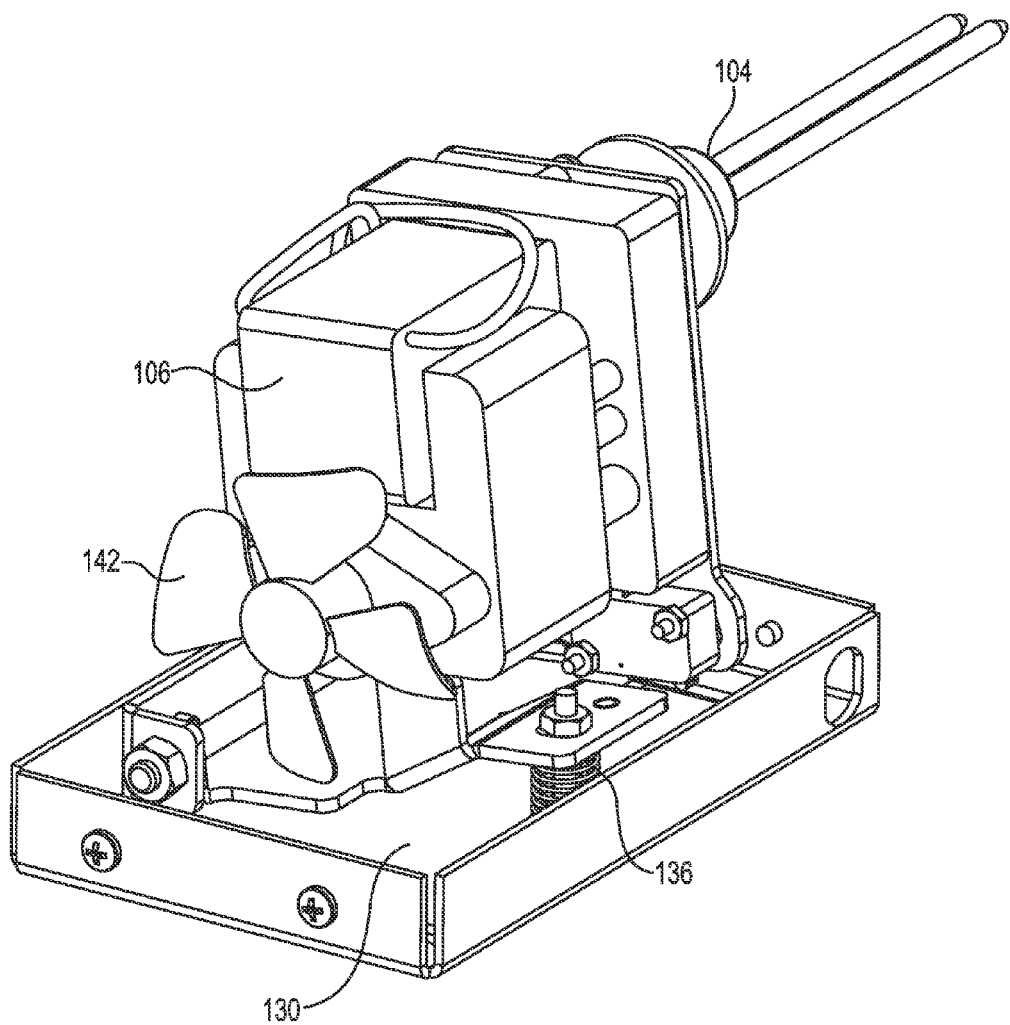
FIG. 7 is a perspective view of a re-wrapping device for animal leg bandages with the top cover removed according to certain example embodiments.
Figure 8:
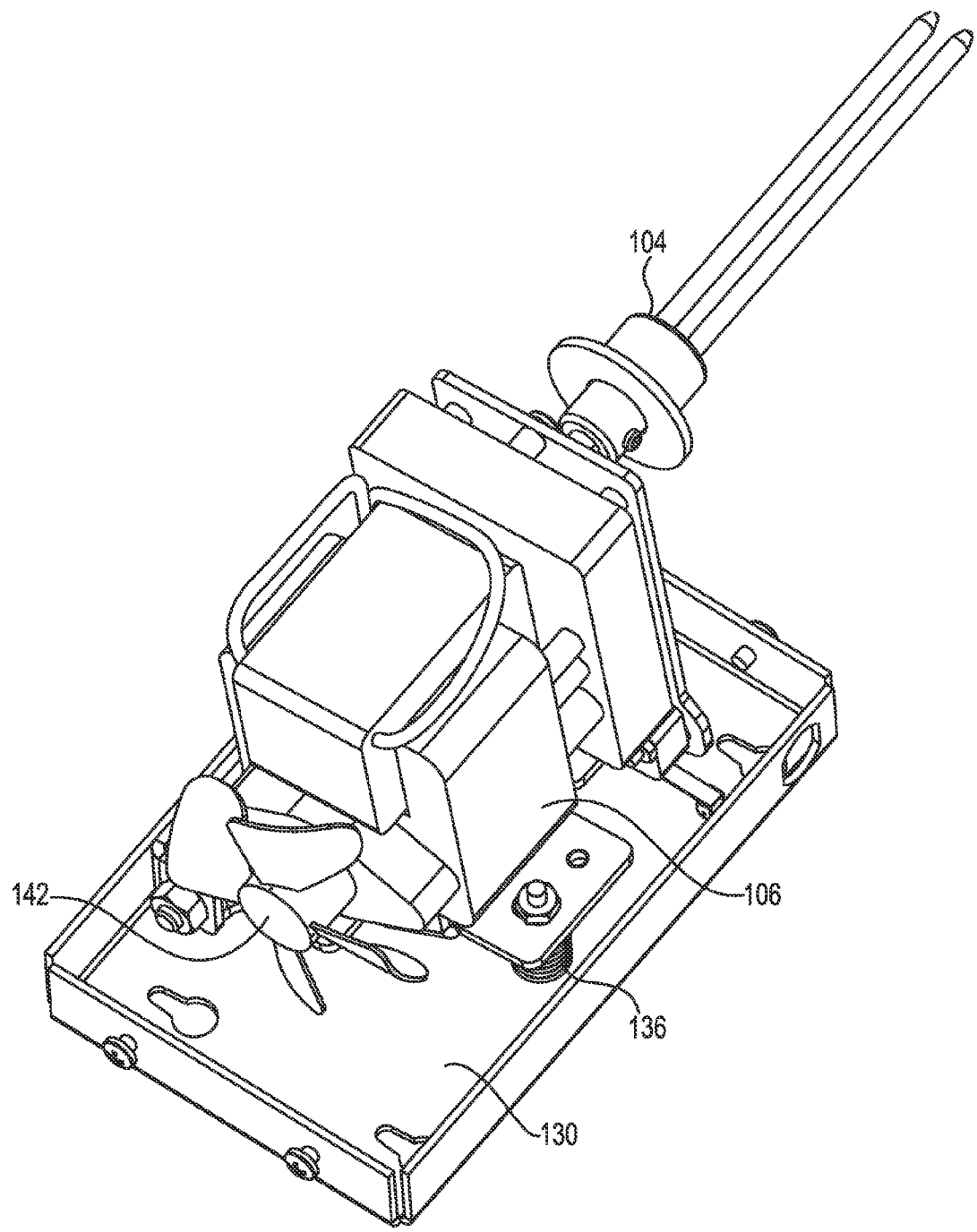
FIG. 8 is a perspective view of a re-wrapping device for animal leg bandages with the top cover removed according to certain example embodiments.

Referring now to FIG. 6, further details of the components of the apparatus will now be described. The electric motor 106 includes an output shaft 108 protruding from a first side. A motor mounting frame 110 is fastened to the motor 106 with a plurality of fasteners (e.g. screws 112) so that the output shaft protrudes through an aperture 114 defined in the motor mounting frame 110.

A spindle 116 is secured to the output shaft 108 and a pair of forks 118 are secured to the spindle 116. The combined spindle 116 and forks 118 will be referred to herein as the spindle assembly 104. A washer 120 can also be disposed over the output shaft 108 and between the mounting frame 110 and the rear side of the spindle 116.

The mounting frame 110 defines a vertical portion 122 and a horizontal portion 124. The horizontal portion 124 defines pivot mount flanges 126 along a first side thereof and an actuator flange 128 on an opposing second side thereof. The side of the mounting frame 110 possessing the mounting flanges 126 can also be designated the pivoting side and the opposing side possessing the actuator flange can be designated the floating side.

Figure 9:
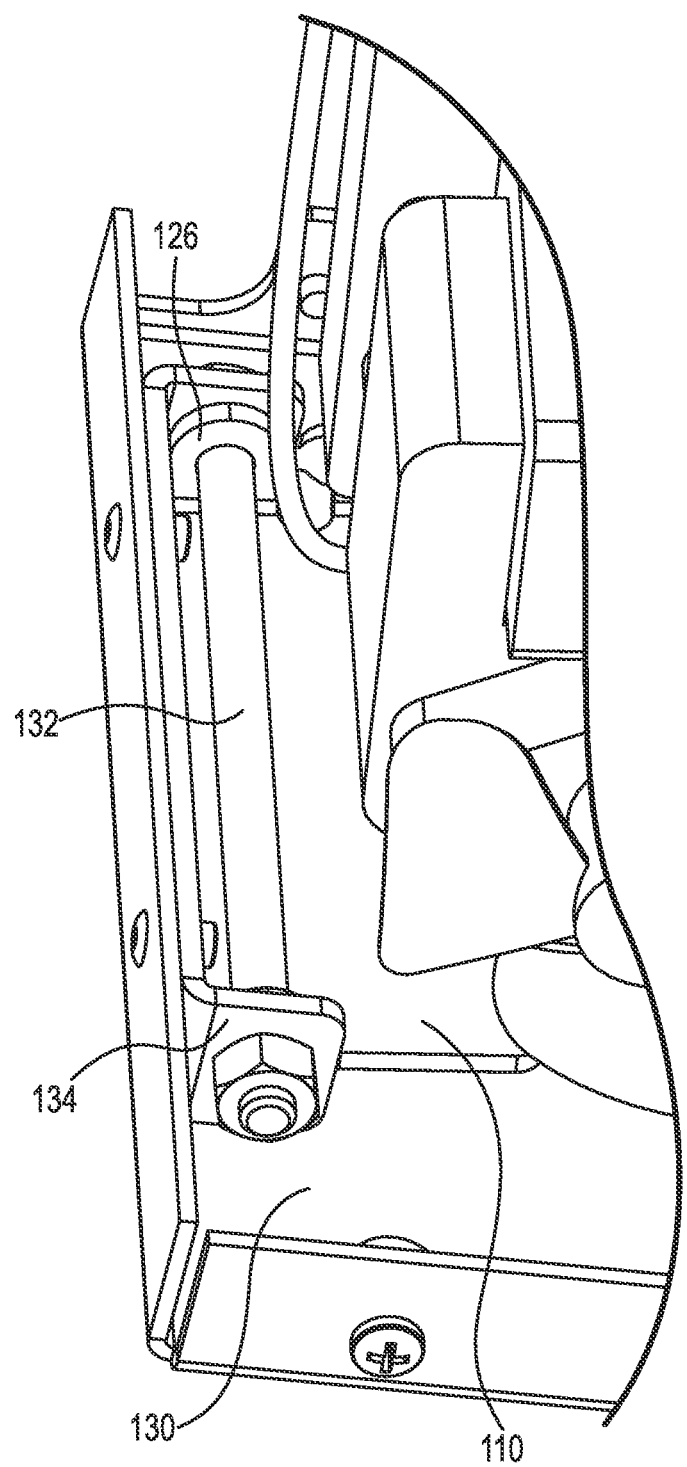
FIG. 9 is a perspective view of a portion of a re-wrapping device for animal leg bandages according to certain example embodiments.
Figure 10:
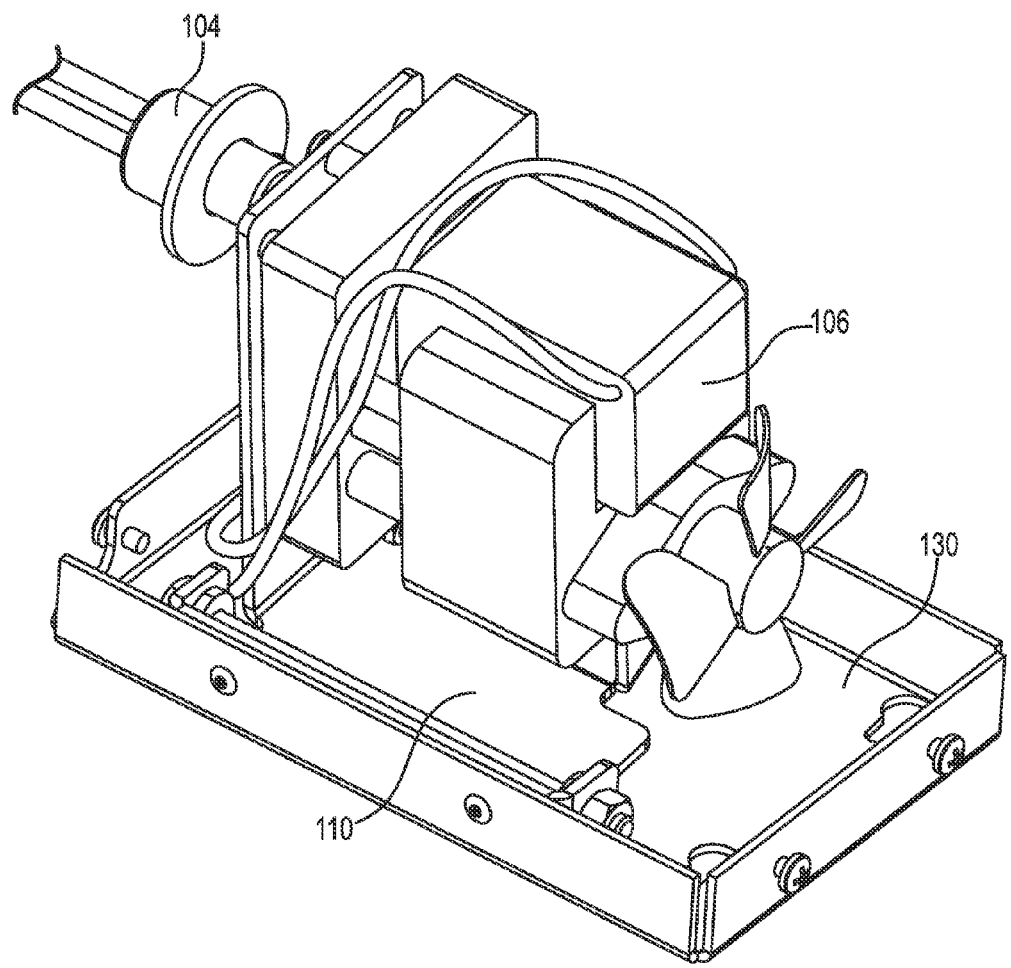
FIG. 10 is a perspective view of a re-wrapping device for animal leg bandages with the top cover removed according to certain example embodiments.
Figure 11:
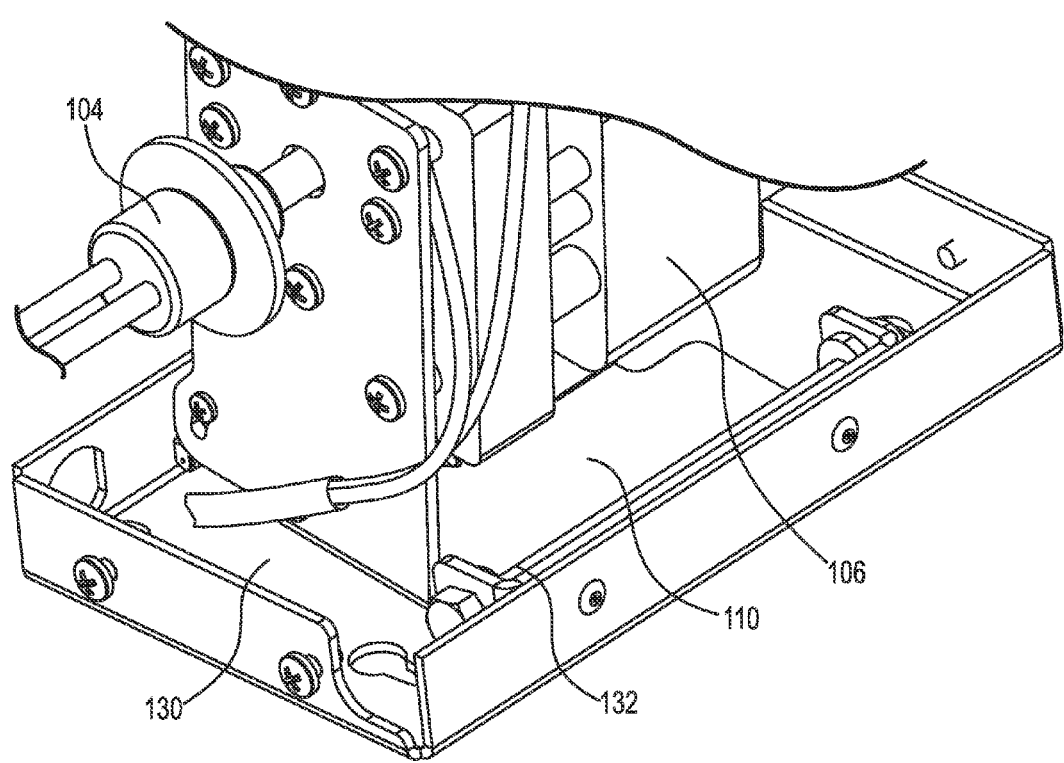
FIG. 11 is a perspective view of a portion of a re-wrapping device for animal leg bandages according to certain example embodiments.
Figure 12:
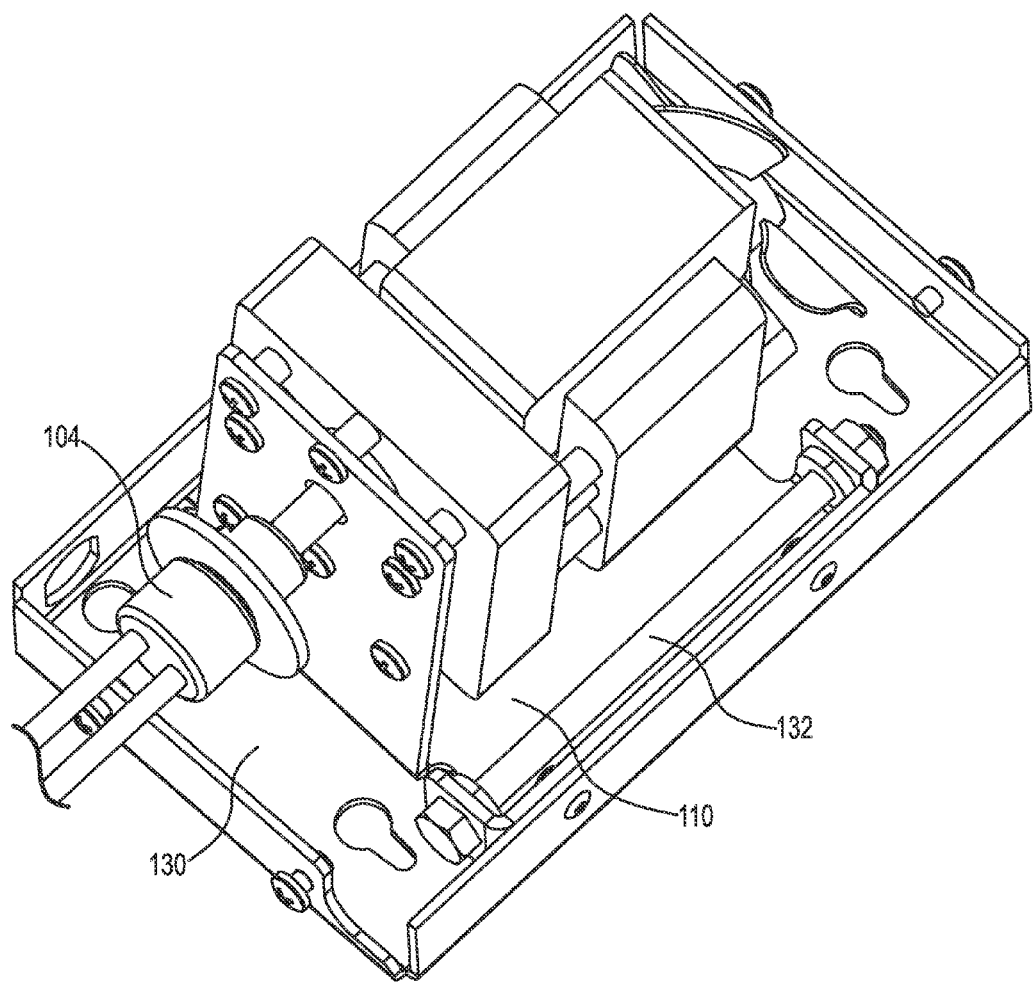
FIG. 12 is a perspective view of a portion of a re-wrapping device for animal leg bandages according to certain example embodiments.
Figure 13:
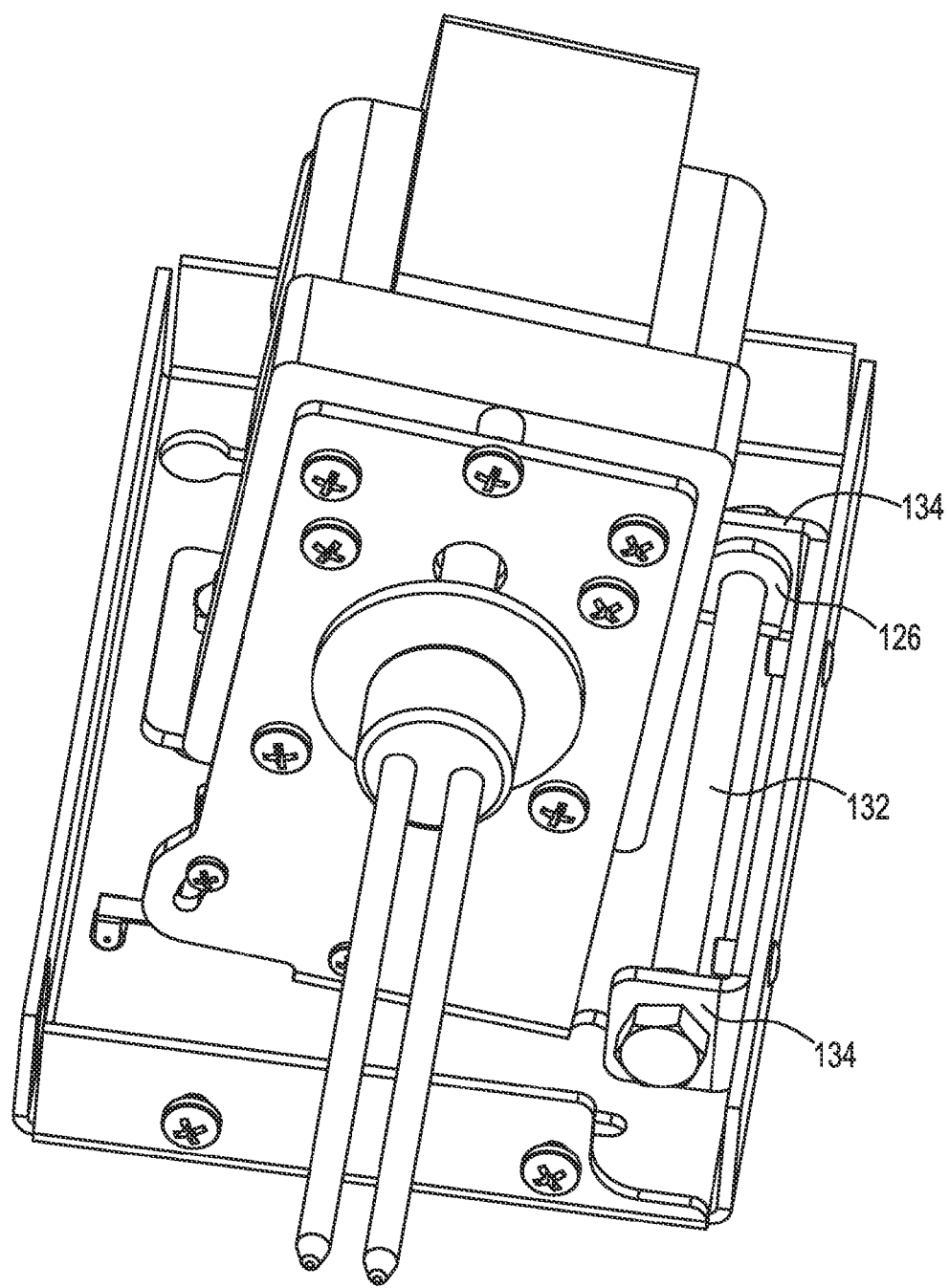
FIG. 13 is a perspective view of a portion of a re-wrapping device for animal leg bandages according to certain example embodiments.

The mounting frame 110 is pivotally mounted to a base plate 130 by a pin 132 engaging the pivot mounting flanges 126 of the mounting frame 110 and securing said flanges 126 to respective pivot mounting flanges 134 provided to the base plate 130. The pin 132 can be secured by a nut or other conventional means. A close-up of this pivotal coupling of the mounting frame 110 to the base plate 130 is shown in FIG. 9.

A spring 136 is disposed vertically between the bottom surface of the actuator flange 128 of the mounting frame 110 and the top surface of the base plate 130. A bolt or other retention means can be disposed through the longitudinal center opening of the spring 136 to secure the spring 136 to one of the base plate 130 or the mounting frame 110. In one embodiment, a bolt is disposed in an upward extending direction though the spring with the bolt head maintained below the bottom of the spring by a washer or nut. Then the opposing or threaded end of the bolt 138 extends through an aperture in the actuator flange 128, and is secured above the flange 128 with a washer and nut. This arrangement allows the spring to be compressed when the motor is pivoted vertically downwards towards the base plate 130, and then to return the motor to the pivoted position away from the base plate in the absence of an applied force, all while limiting the travel of the motor between these two end positions.

An activation switch 140 is disposed on the motor, the motor housing or the mounting frame such that the switch 140 is actuated to complete an electrical circuit and turn on the motor when the spring 130 is compressed. Then the switch opens the circuit to deactivate the motor when the spring expands or decompresses. Thus, it can be appreciated that applying a force in a direction normal to the longitudinal length of the forks 118 will cause the motor to pivot towards the base plate 130, thereby compressing the spring 136 and activating the switch 140 to turn the motor 106 on. Releasing or ceasing application of the activation force will cause the spring 136 to return the motor 106 to the extended position and turn off the motor.

The winding apparatus can be mounted to a surface using a wall mounting plate 144, which is shown in detail in FIG. 6. Mounting fasteners (e.g. screws 146) are illustrated in FIGS. 3-6. The wall mounting plate 144 is mounted to either a vertical surface or to a horizontal surface. Thus, when mounted to a vertical surface, a vertically downward force applied to the bandage engaged with the forked spindle 104 will turn the motor on. On a horizontal surface, a force component towards the user in the horizontal plane is applied to the bandage engaged with the forked spindle 104 to turn the motor on. In either case, releasing tension on the bandage will turn the motor off automatically.

FIGS. 7-8 and 10-13 provide illustrations of the assembled wrapping device with the cover 102 removed. Note that the spring 136 is shown in the extended or uncompressed state. Thus, the motor 106 is off in this depiction.

The fan 142 shown throughout these embodiments is optionally provided to cool the motor 106 and the interior of the housing 102.

One type of suitable motor 106 is a Rex Engineering E69477 Gear Motor, 115V/60 Hz, 5.75:1 Ratio, 1 inch×⅝₁₆ inch shaft with fan. This is a shaded pole motor which is AC powered and runs in only one direction. The output speed is variable from 2-500 rpm. The output torque is 50 inch-pounds and has built-in thermal protection with auto-reset. Preferred operating RPM range is from 80-100 rpm.

The motor can operate using 120V AC, 240V AC or 24V AC, or other suitable current, or by battery power, or by a combination thereof. While the motor in one embodiment is powered by conventional household AC power via a cord and conventional plug. In other embodiments, a rechargeable onboard battery can be used to power the motor. In yet another embodiment, the motor can be operated via either or both of the onboard battery and conventional household current.

Figure 14:
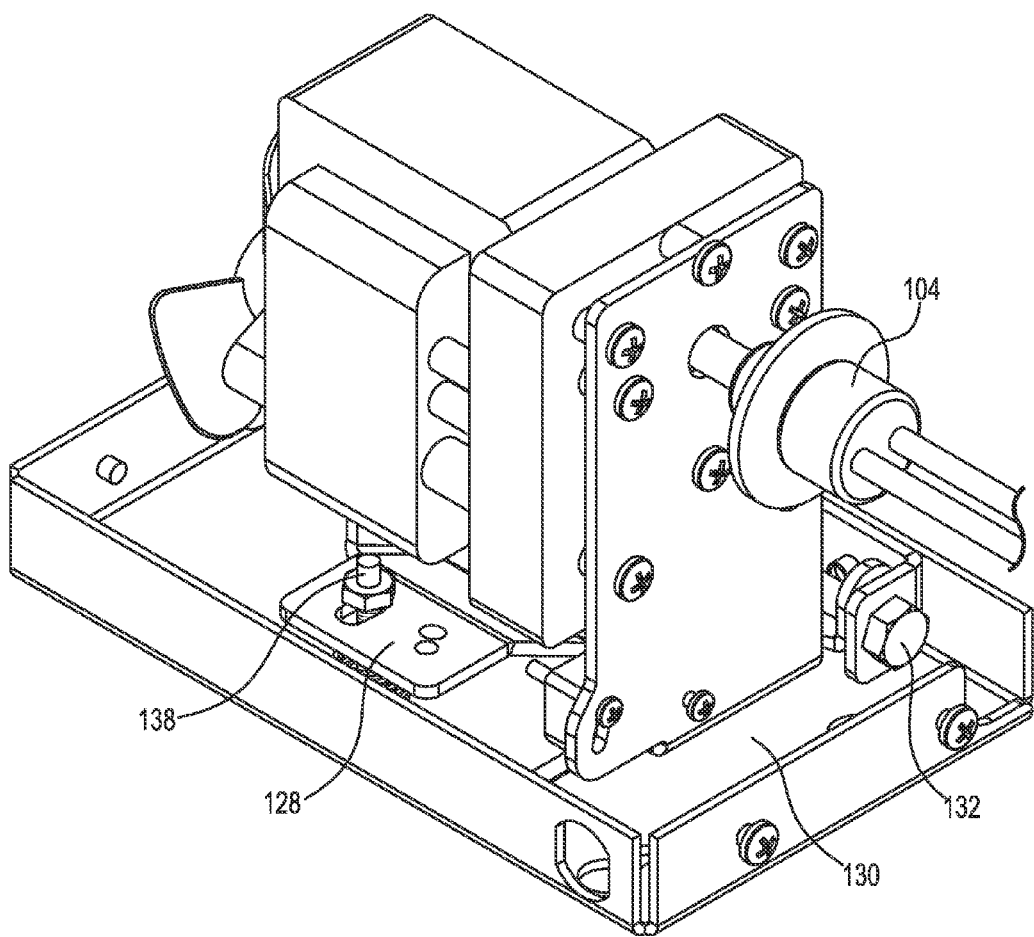
FIG. 14 is a perspective view of a re-wrapping device for animal leg bandages according to certain example embodiments.
Figure 15:
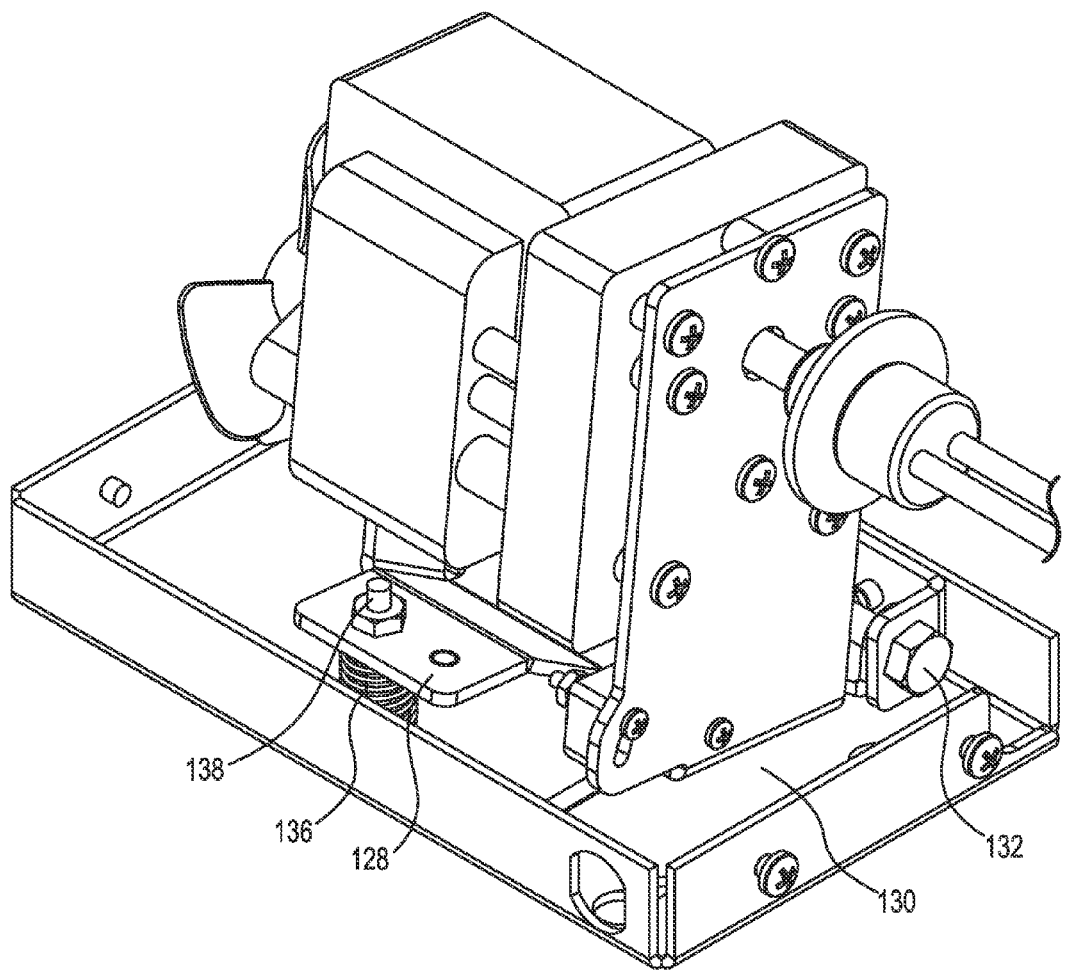
FIG. 15 is a perspective view of a re-wrapping device for animal leg bandages according to certain example embodiments.
Figure 16:
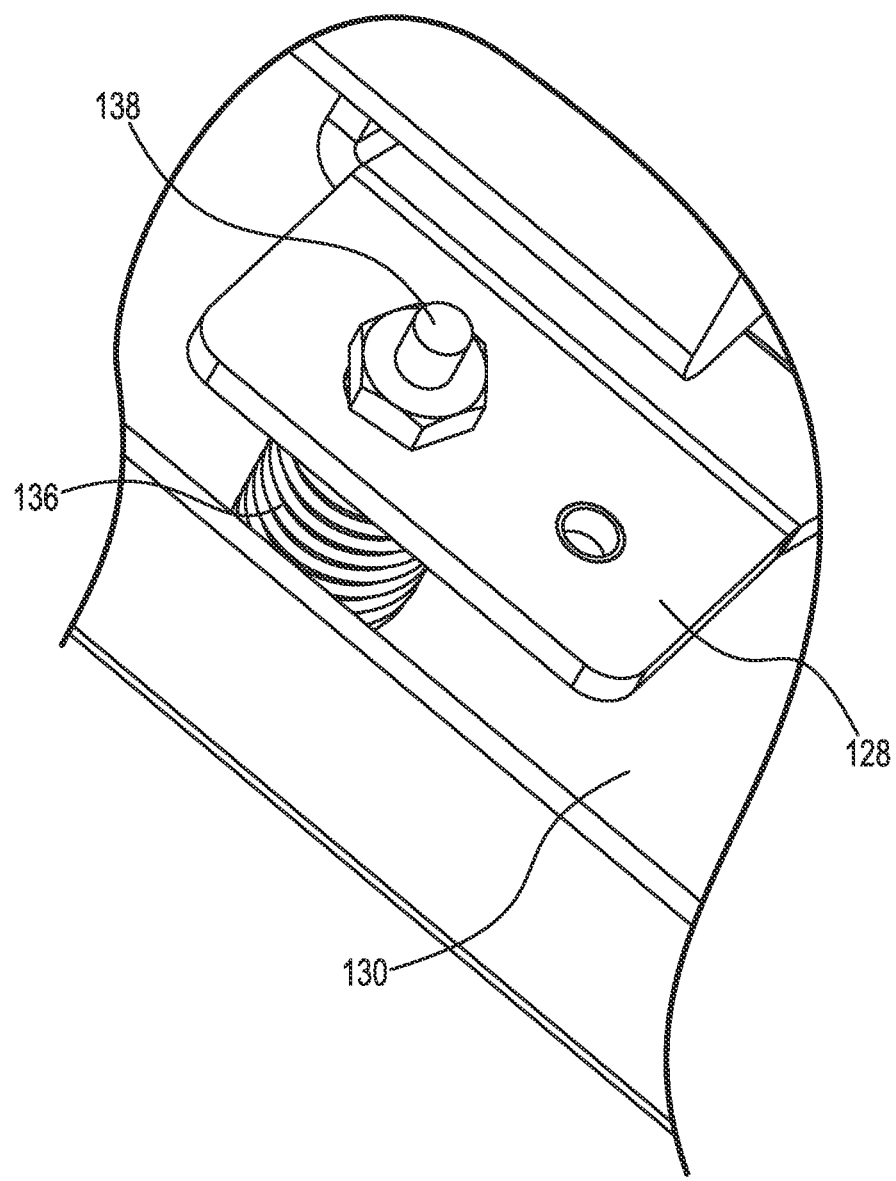
FIG. 16 is a perspective view of a portion of a re-wrapping device for animal leg bandages according to certain example embodiments.

FIGS. 14-15 illustrate the motor in the activated and deactivated position, respectively. In FIG. 14, the spring 136 is compressed toward the base plate 130. In FIG. 15, the spring is uncompressed, so the spring is at its maximum travel as limited by the spring retention bolt 138 and its respective fastener. A close-up of the spring 136 fastened to the actuator flange 128 by the spring retention bolt 138 is provided in FIG. 16. Note that only one spring is illustrated, but two or more springs can be provided without departing from the scope of the invention. In addition, other resilient or biasing means such as compressible rubber gaskets, air and other fluid-filled bladders, etc. can be used instead of, or in addition to, the spring in alternative embodiments.

Figure 17:
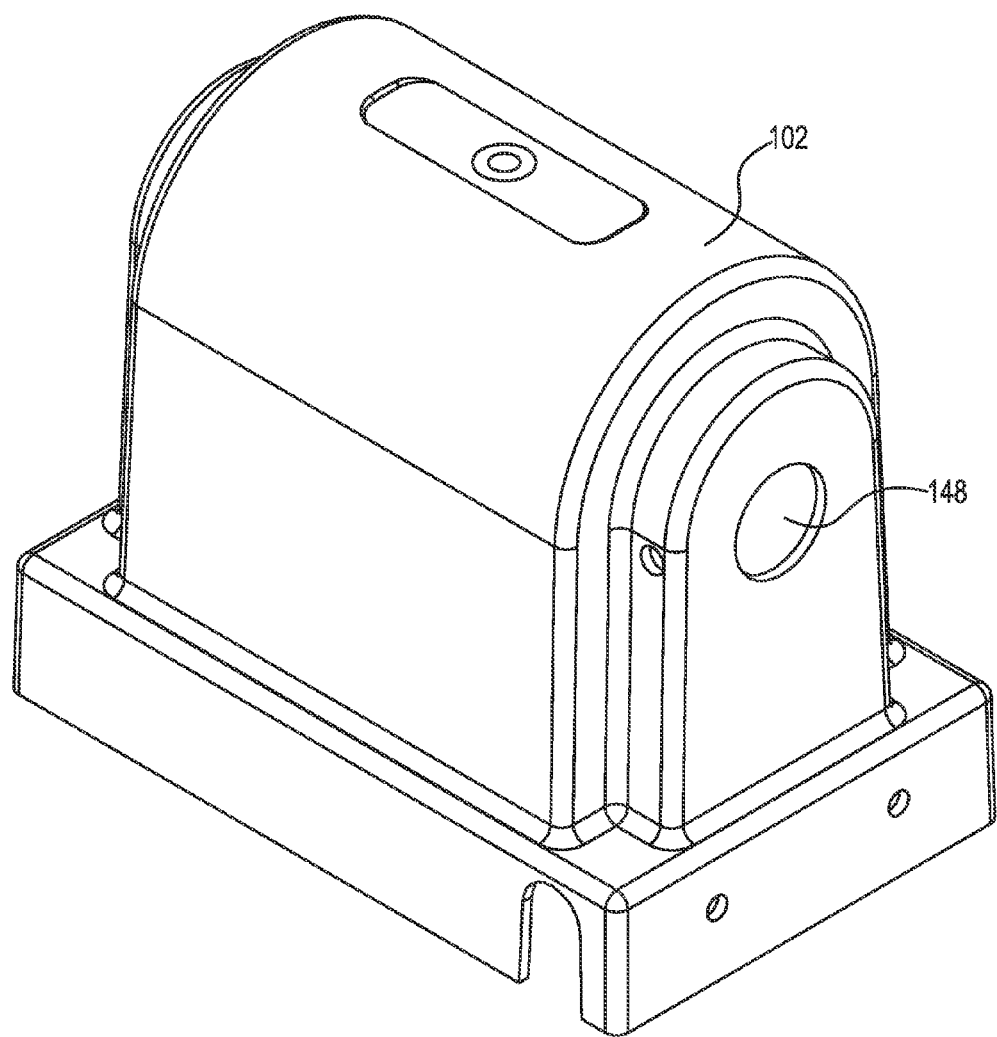
FIG. 17 is a perspective view of a top cover of a re-wrapping device for animal leg bandages according to certain example embodiments.
Figure 18:
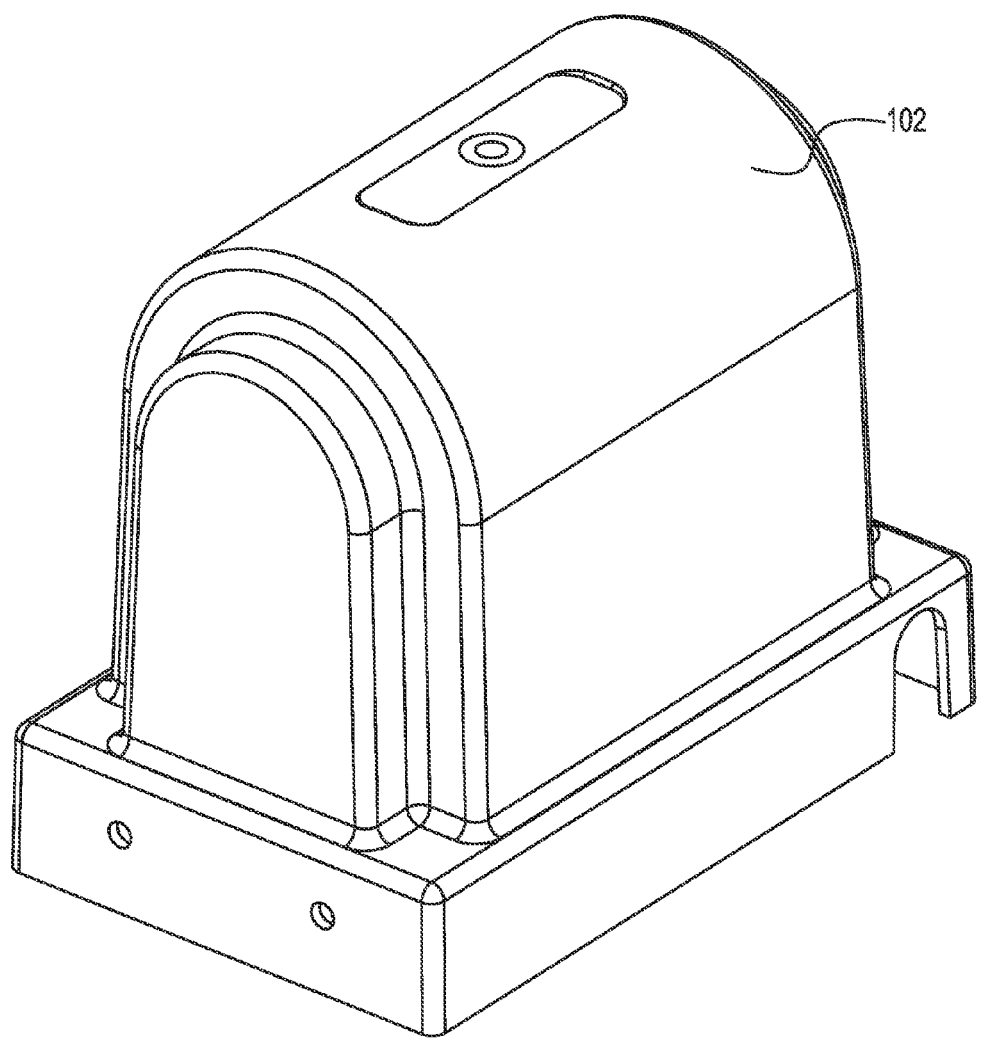
FIG. 18 is another perspective view of a top cover of a re-wrapping device for animal leg bandages according to certain example embodiments.

FIGS. 17-18 depict the housing 102 of the apparatus. The housing defines an outer enclosure having an open interior. The housing possesses an open bottom side that fits over the base plate 130. Screw holes on front and back sides can be used to secure the housing to the base plate with a plurality of screws, bolts or other fastening means. A first side of the enclosure includes a spindle aperture 148 to allow the spindle 116 of the spindle assembly 104 to protrude through the housing. The diameter of the spindle aperture 148 is larger than the spindle's diameter (or appropriately shaped) so that the spindle can move freely (i.e. has clearance) as the pivot spring is fully compressed and decompressed.

Note that the preferred housing 102 is plastic, but can be formed of any suitable material, including metal. When mounted on a vertical surface, the housing 102 provides a surface for resting complete rewrapped bandage spools.

Figure 19:
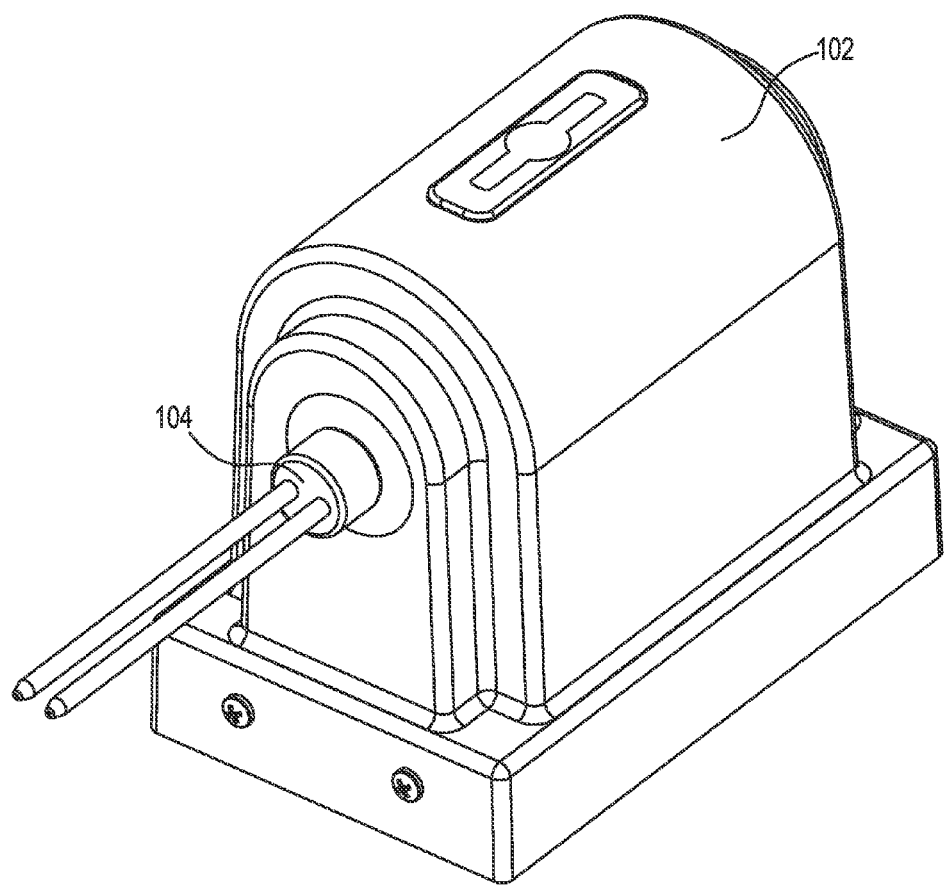
FIG. 19 is a perspective view of a portion of a re-wrapping device for animal leg bandages according to certain example embodiments.
Figure 20:
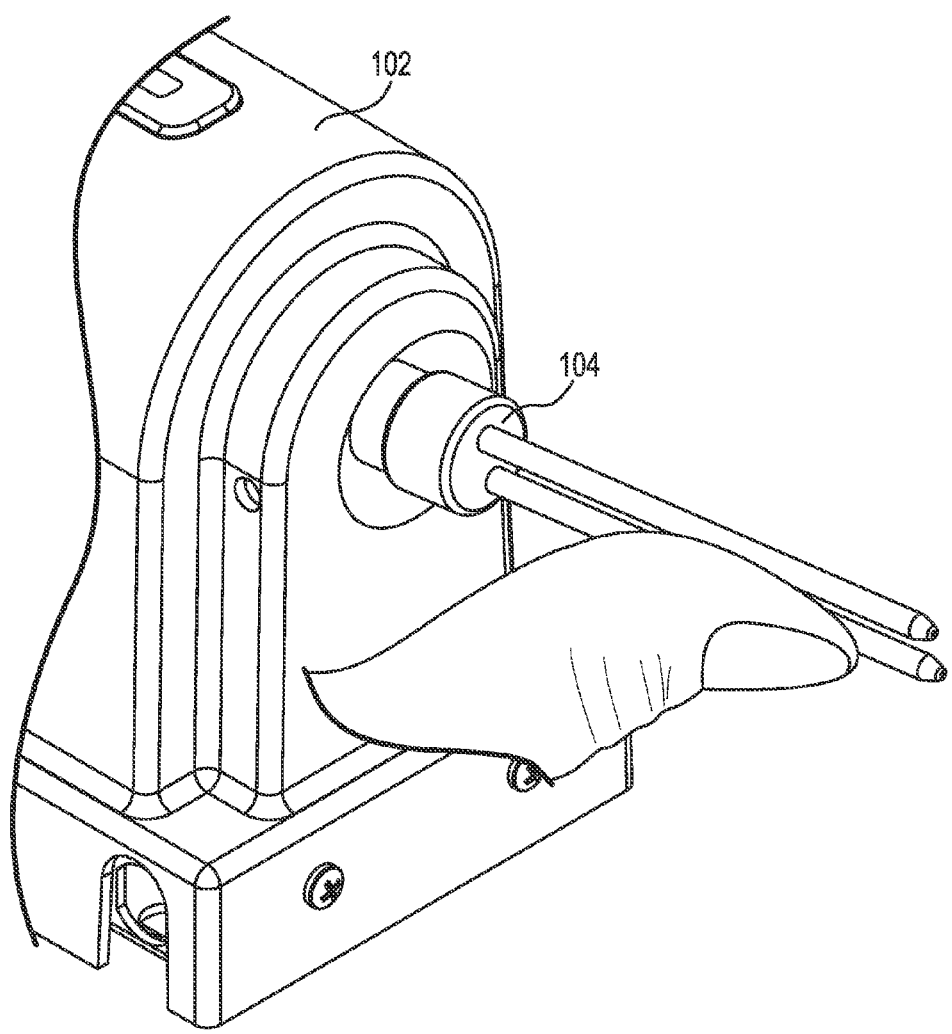
FIG. 20 is a perspective view of a portion of a re-wrapping device for animal leg bandages with pressure applied to the spindle according to certain example embodiments.

FIG. 19 shows the assembled wrapping device 100 in the "off" position. Then when pressure is applied to the forks 118 as indicated by the thumb in FIG. 20, the motor and other components mounted to the mounting frame pivot slightly as the pivot spring compresses and the motor is turned on. Of course, in use, the pressure is applied by pulling slightly on the bandage to be wrapped, not by an actual thumb of the user.

In use, the user first engages one end of the equine bandage with the forks 118 of the spindle assembly 104. Then, the user tugs downward or toward themselves (depending on the orientation in which the apparatus is mounted) to activate the motor 106. This activation system and method leaves both hands available to guide the equine bandage as the bandage is rolled up on the forked spindle assembly 104. When the opposing end of the bandage is reached, the pressure maintaining the motor in the "on" position ceases because there is nothing for the user left to grasp. Thus, the motor automatically turns "off." The user then removes the wrapped bandage spool by sliding it longitudinally off of the forks 118.

It should be noted that the tension in the wrapped bandage can be adjusted by the user by adjusting how hard the user tugs on the bandage with their hands as it wraps up on the spindle. This allows the user to simply and easily achieve desired re-wrap tightness without the need to adjust the operation of the device.

The amount of pressure required to turn the motor on and off is controlled by the spring compression force. Preferably the compression force is selected such that a slight tension is placed on the bandage, but not so much that the bandage is appreciably tensioned while wrapping. This selection of the turn on/off force thus allows the user to wrap the bandage very loose, very tight or anywhere in between as the user desires merely by how hard they pull on the bandage while it winds up.

The wrapping device can optionally be provided with a master override OFF switch (not shown) that will prevent the wrapping device from being activated in the conventional matter if the override switch is in the off state. Such switch is preferably provided to a portion of the outer housing.

The wall mounting plate 144 can be configured so that it is separately mounted to a vertical or horizontal surface. Then the plate can be removably attached to the mounting plate assembly, so that it can slide and lock onto a permanent or temporary mounting position as the user may desire. This functionality can be provided, for example, as shown in FIG. 6, by the protruding pins 150 on the mounting plate 144 and the respective locking apertures 152 defined in the base plate 130. In other alternative embodiments, a hanging bracket can be provided for securing the base of the device to a temporary location, such as over a wood beam. Securing the base plate 130 to the hanging bracket can be provided in the same manner as shown in FIG. 6.

The wrapping apparatus can be configured to be free from external levers and switches. Such external levers and switches create points of potential failure and can present dangers to operators, animals, clothing, equipment, etc. since they may snag, catch and abrade when contacting the device.

The various brackets, plates and fastening hardware are preferably formed of metal, but other suitable materials can be used without departing from the scope of the invention.

The forks 118 depicted in the figures are elongated cylinders extending parallel to one another and including tapered ends. The tapered free ends facilitate the introduction and removal of the equine bandage with the forked spindle assembly 104. The forks 118 need not be parallel to one another. One of the forks can converge towards the other either in a straight line or in a curved manner as the forks go from the base to the tips. Both forks 118 can converge towards each other as well as they extend towards their respective free ends.

Other then the tapered ends, the forks 118 are shown to have a constant diameter. However, the forks 118 can be curved and/or have varied diameters along their lengths to facilitate self centering of the bandage as it is would. The cross-section also need not be circular, but can be, semi-circular, polygonal, or another complex shape. The 118 forks can be formed of metal, plastic, carbon fiber, or other rigid material.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An equine bandage wrapping device, comprising:
    a base plate;
    a frame mounting plate pivotally coupled to the base plate and including a first side pinned to the base plate and an opposing free side, wherein the free side is pivotable between a first position and a second position;
    a spring disposed between the base plate and the frame mounting plate, wherein the spring is compressed when the frame mounting plate pivots from the first position to the second position;
    an electric motor disposed on the frame mounting plate, wherein a long axis of the motor is parallel to the first side of the frame mounting plate;
    a switch electrically coupled to the motor and mechanically coupled to the frame mounting plate such that the switch is closed to complete an electrical circuit and turn on the electric motor when the frame mounting plate pivots from the first position to the second position and such that the switch is activated to open an electric circuit which turns off the electric motor when the spring is uncompressed due to pivoting of the frame mounting plate from the second position to the first position; and
    a forked spindle assembly coupled to the electric motor that is configured to wind up an equine bandage as the motor turns.

2. The device of claim 1, wherein the forked spindle assembly comprises a spindle and a pair of elongated forks secured to the spindle, wherein each form comprises a first end that is secured to the spindle and an opposing free second end.

3. The device of claim 2, wherein each fork in the pair of forks comprises an elongated cylinder, and wherein the free second end of each fork in the pair of forks is tapered.

4. The device of claim 2, wherein the pair of forks converge towards one another as they extend away from the spindle.

5. The device of claim 1, wherein the frame mounting plate is pivotally coupled to the base plate such that application of a force in a direction normal to the forked spindle assembly pivots the frame mounting plate to actuate the switch.

6. The device of claim 5, wherein the frame mounting plate is pivotally coupled to the base plate such that removing application of the force in the direction normal to the forked spindle assembly allows the spring to pivot the frame mounting plate to deactivate the switch.

7. The device of claim 1, further comprising a housing disposed over the base plate to define an enclosed space between the housing and base plate, wherein at least a portion of the forked spindle assembly protrudes from the housing.

8. The device of claim 7, wherein the forked spindle assembly protrudes though an aperture defined in a sidewall of the housing, wherein the aperture has a diameter that is larger than a diameter of the forked spindle assembly.

9. The device of claim 7, wherein the device is free of any switches disposed outside of the enclosed space.

10. The device of claim 1, further comprising a wall mounting plate configured to releasably secure to the base plate.

11. A method of wrapping an elongated bandage having first and second opposing ends, the method comprising:
engaging the bandage with a forked spindle adjacent a first end of the bandage;
applying a tension force to the bandage to cause a motor to pivot about a long axis of a first side of a mounting frame plate with the first side having a long axis parallel to a long axis of the motor, wherein the pivoting actuates the motor to rotate the forked spindle; and
withdrawing the tension force from the bandage to stop the motor from rotating the forked spindle.

12. The method of claim 11, wherein the tension force is withdrawn from the bandage when the bandage is finished winding up into a spool on the forked spindle.

13. The method of claim 11, wherein applying the tension force to the bandage is in a direction normal to an axis of rotation of the forked spindle.

14. The method of claim 11, wherein applying the tension force to the bandage causes a motor mounting frame to pivot about an axis that is parallel to an axis of rotation of the forked spindle.

15. The method of claim 11, wherein applying the tension force to the bandage causes a pressure switch to close an electrical circuit that provides power to the motor.

16. The method of claim 11, wherein withdrawing the tension force to the bandage causes a pressure switch to open an electrical circuit that provides power to the motor.

17. The method of claim 11, further comprising disposing the motor inside of an enclosure such that at least a portion of the forked spindle protrudes from the enclosure.

18. The method of claim 17, further comprising mounting the enclosure on a vertical surface and applying the tension of the bandage in a downward vertical direction.

19. An equine bandage wrapping system, comprising:
a base plate;
a frame mounting plate pivotally coupled to the base plate and including a first side pinned to the base plate and an opposing free side, wherein the free side is pivotal toward and away from the base plate;
a resilient means disposed between the base plate and the frame mounting plate for biasing the free side of the frame mounting plate away from the base plate;
an electric motor disposed on the frame mounting plate, wherein a long axis of the motor is parallel to the first side of the frame mounting plate;
a switch electrically coupled to the motor and mechanically coupled to the frame mounting plate such that the switch is activated to complete an electrical circuit and turn on the electric motor when the free end of the frame mounting plate pivots towards the base plate and such that the switch is deactivated to open an electric circuit to turn off the electric motor when the free end of the frame mounting plate pivots away from the base plate;
a forked spindle assembly coupled to the electric motor that is configured to wind up an equine bandage as the motor turns; and
a housing disposed over the base plate that encloses the motor, the switch, the resilient means and the frame mounting plate,
wherein at least a portion of the forked spindle assembly externally protrudes from the housing.

20. The device of claim 19, wherein the frame mounting plate is pivotally coupled to the base plate such that application of a force in a direction normal to the forked spindle assembly pivots the frame mounting plate to compress the resilient means.

* * * * *